United States Patent [19]

Kawamatsu et al.

[11] 4,348,403
[45] Sep. 7, 1982

[54] 2-AMINO-4-(4-BENZYLOXYPHENYL)-THIAZOLES, AND THEIR USE IN HYPERLIPEMIA

[75] Inventors: Yutaka Kawamatsu, Kyoto; Takashi Sohda, Takatsuki; Yoshio Imai, Kawanishi, all of Japan

[73] Assignee: Takeda Chemical Industries, Ltd., Osaka, Japan

[21] Appl. No.: 197,755

[22] Filed: Oct. 16, 1980

[30] Foreign Application Priority Data

Oct. 17, 1979 [JP] Japan .............................. 54/134489

[51] Int. Cl.³ ................. A61K 31/425; C07D 277/40; C07D 277/42; C07D 277/46
[52] U.S. Cl. .................................... 424/270; 548/193; 548/195
[58] Field of Search ................. 548/193, 195; 424/270

[56] References Cited

U.S. PATENT DOCUMENTS

| | | | |
|---|---|---|---|
| 1,743,083 | 1/1930 | Johnson | 548/193 |
| 3,775,425 | 11/1973 | Bosshard et al. | 548/193 |
| 4,074,057 | 2/1978 | Kawamatsu et al. | 560/55 |
| 4,080,505 | 3/1978 | Kawamatsu et al. | 560/55 |

Primary Examiner—Alton D. Rollins
Attorney, Agent, or Firm—Wenderoth, Lind & Ponack

[57] ABSTRACT

2-Amino-4-(4-benzyloxyphenyl)thiazole compounds of the formula:

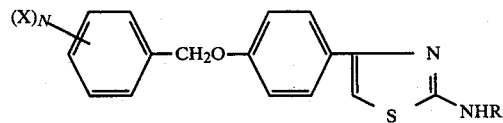

wherein X is hydrogen, a halogen, a lower alkyl having 1 to 4 carbon atoms or trifluoromethyl; R is hydrogen, a lower alkyl having 1 to 4 carbon atoms, a lower alkenyl having 2 to 4 carbon atoms or a carboxylic acyl having 1 to 6 carbon atoms; and n is 1 or 2, or pharmaceutically acceptable salts thereof, are novel compounds and are useful as a prophylactic agent or therapeutic agent against hyperlipemia in mammals including human beings.

8 Claims, No Drawings

2-AMINO-4-(4-BENZYLOXYPHENYL)-THIAZOLES, AND THEIR USE IN HYPERLIPEMIA

The present invention relates to novel thiazole derivatives, a process for producing the same, and a pharmaceutical composition containing the same as an active component.

More particularly, the present invention relates to:
1. A thiazole derivative of the formula:

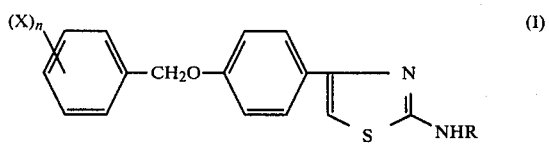

wherein X is hydrogen, a halogen, a lower alkyl having 1 to 4 carbon atoms or trifluoromethyl; R is hydrogen, a lower alkyl having 1 to 4 carbon atoms, a lower alkenyl having 2 to 4 carbon atoms or a lower carboxylic acyl having 1 to 6 carbon atoms; and n is 1 or 2, or a pharmaceutically acceptable salt thereof, 2. A process for producing a thiazole derivative of the formula (I) or a pharmaceutically acceptable salt thereof, which comprises reacting a compound of the formula:

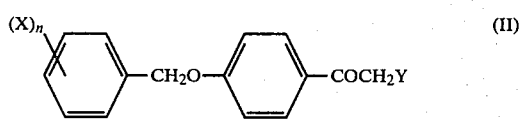

wherein X and n have the meanings given above and Y is a halogen, with a compound of the formula:

wherein R has the meaning given above, and

3. A pharmaceutical composition which contains an effective amount for the theraphy of hyperlipemia in mammals of a compound of the formula (I) or a pharmaceutically acceptable salt thereof, and a pharmaceutically acceptable carrier, vehicle or diluent therefor.

Referring to the groups represented by R in the general formulas (I) and (III), as examples of the lower alkyl having 1 to 4 carbon atoms there may be mentioned straight-chain or branched-chain alkyl such as methyl, ethyl, n-propyl, i-propyl, n-butyl, i-butyl and t-butyl; examples of the lower alkenyl having 2 to 4 carbon atoms include vinyl and allyl; and as examples of the lower carboxylic acyl having 1 to 6 carbon atoms there may be mentioned formyl and alkylcarbonyl having 2 to 6 carbon atoms such as acetyl, propionyl, butyryl and pivaloyl. With reference to the groups represented by X in the general formulas (I) and (II), examples of the halogen atom may include fluorine, chlorine, etc., and as examples of the lower alkyl having 1 to 4 carbon atoms there may be mentioned straight-chain or branched-chain alkyl such as methyl, ethyl, n-propyl, i-propyl and n-butyl.

The compounds of this invention may assume two tautomeric forms by the tautomerization depicted below

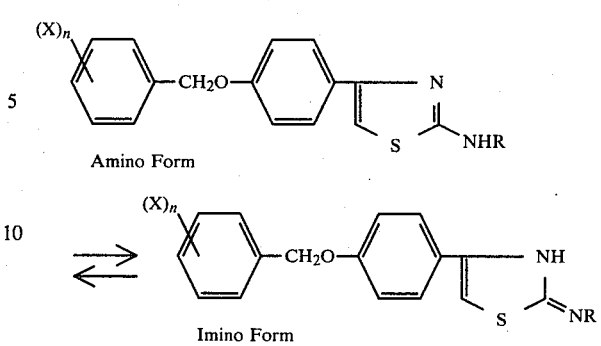

[wherein each symbol has the meaning given above]. Therefore, the compounds of this invention may be designated by either of these alternative systems or the corresponding nomenclature thereof. In this specification and the claims appended hereto, however, all the compounds of this invention are designated by their amino form. This invention should be construed to cover all the above tautomers.

The compound of this invention represented by the formula (I) may form a great variety of pharmaceutically acceptable salts. The compound where the group designated by R is for example hydrogen or lower alkyl can be allowed to form for example salts with hydrochloric acid, sulfuric acid, hydrobromic acid, maleic acid, fumaric acid, succinic acid, etc.

The present compound (I) can take various crystal forms. For example, the hydrochloride of 2-amino-4-[4-(4-chlorobenzyloxy)phenyl]thiazole takes at least 4 crystal forms as shown in example 1-a, and 2-amino-4-[4-(4-chlorobenzyloxy)phenyl]thiazole can take at least 3 crystal forms as shown in example 1-b.

The thiazole compounds (I) of the present invention, with their characteristic feature that, in hypercholesterolemia of rats (dietetic-hypercholesterolemia susceptible rats obtained through repeating the selective brother-sister mating), they decrease the plasma cholesterol level, while they increase both the high-density lipoprotein (HDL) and its major apolipoprotein which is Apo A-1, are expected to be of value for treatment and prevention of hyperlipemia in mammals, including human beings.

When the compound of this invention is used for such medicinal purposes, it can be orally or parenterally administered either as it is or in admixture with suitable pharmaceutically acceptable carriers, vehicles or diluents in such dosage forms as powders, granules, tablets, capsules, pellets, injections, suppositories, etc. In the case of being employed as a therapeutic or prophylactic agent for the above-mentioned disease, the compound can be orally or parenterally administered normally in the daily dose of 1 mg to 500 mg, preferably 15 mg to 150 mg, for an adult.

The thiazole derivative (I) of the present invention can be produced by reacting a compound of the general formula (II) with a compound of the general formula (III). The reaction of the compound (II) with the compound (III) is normally conducted in a solvent. As examples of the solvent, there may be mentioned alcohols such as methanol, ethanol, propanol, butanol, ethylene glycol monomethyl ether, etc., and ethers such as tetrahydrofuran and dioxane as well as acetone, dimethylsulfoxide, sulfolane, and others. The ratio of the starting compounds is not specifically restricted, although it is preferable to employ the compound (III) in slight excess of the equimolar amount against the compound (II). Preferably, the compound (III) is employed in the proportion of 1 to 2 moles against 1 mole of the compound (II). The reaction conditions such as reaction temperature and reaction time vary depending for example upon the starting compounds and solvent to be employed, and the reaction is normally conducted at room temperature or at the boiling point of solvent for a period of time within the range of 30 minutes to 24 hours.

The thiazole compound (I) of the present invention, furthermore, can also be produced by the following procedure. Thus, a compound of the general formula:

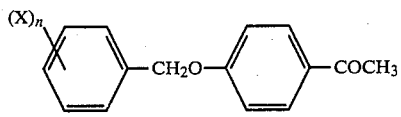
(IV)

[wherein the symbols each are as defined hereinbefore] is reacted with a compound of the general formula (III) in the presence of sulfuryl chloride to thus obtain the thiazole derivative (I). The ratio of the starting compounds is not specifically restricted, although it is desirable to normally employ compound (III) in excess of the equimolar amount against the compound (IV). Preferably, the thiourea compound (III) is employed in the proportion of 1 to 2 moles against 1 mole of the compound (IV). Moreover, sulfuryl chloride is preferably employed in the amount of not less than 1 mole against one mole of compound (IV). The reaction conditions such as reaction temperature and reaction time vary depending upon type and amount of the starting compounds to be employed, and, because the reaction is normally an exothermic one, the addition of sulfuryl chloride is suitably controlled in conformity with the exothermic state. The reaction medium liquefies and then solidifies. After such state is attained, the medium is further heated at 100° to 120° C. for 1 to several hours.

The thiazole derivatives obtained in this manner present the acid salt form, except for the case where R is a lower carboxylic acyl group. They may be isolated as they stand, although they, if necessary, may be isolated as free amines by treating them with a suitable base such as aqueous ammonia and an aqueous solution of sodium bicarbonate, sodium carbonate, potassium carbonate, etc. Furthermore, these free amine forms can be converted back to a suitable acid salt. In addition, it is possible to convert the free amines to other thiazole derivatives (I) by acylating them with a suitable acylating agent. Employable as the acylating agent are, for example, carboxylic acid chlorides such as acetyl chloride and propionyl chloride or carboxylic acid anhydrides such as acetic anhydride and propionic anhydride. The acylation reaction is normally conducted in a solvent and in the presence of a base, if necessary. As examples of the solvent there may be mentioned aromatic hydrocarbons such as benzene and toluene, and ethers such as ether, dioxane and tetrahydrofuran, as well as pyridine, dimethylformamide, dimethylsulfoxide, etc. Examples of the base may include sodium carbonate, potassium carbonate, sodium hydroxide and potassium hydroxide as well as tertiary amines such as triethylamine and pyridine. The ratio of the starting compounds is not specifically restricted, although it is normally desirable to employ the acylating agent in slight excess of the equimolar amount against the free amine. The base which is employed if necessary is normally used in the equimolar amount or the equal gram equivalent against the free amine. The reaction conditions such as reaction temperature and reaction time vary depending for example upon the starting compound and solvent to be employed, and the reaction is normally carried out at a temperature within the range of room temperature to 100° C. for a period of time in the region of 30 minutes to 24 hours.

The thiazole derivatives (I) obtained by the above procedure can be isolated and purified by separatory procedures conventional per se such as concentration, in-vacuo concentration, solvent extraction, crystallization, recrystallization, phasic transfer and chromatography.

Examples are given below to illustrate the present invention more specifically.

EXAMPLE 1

(a) A 8.0 g portion of 4-(4-chlorobenzyloxy)phenacyl chloride and 2.3 g of thiourea were stirred in 70 ml of ethanol under reflux for 1 hour. After cooling, 100 ml of ether was added, and the precipitating crystals were recovered by filtration, resulting in 7.8 g (82.1%) of hydrochloride of 2-amino-4-[4-(4-chlorobenzyloxy)phenyl]thiazole. Recrystallized from 80% ethanol m.p., 248°–250° C.

The product obtained above can take at least 4 crystal forms. The X-ray diffraction pattern of the product measured by the powder method is as shown below.

Form I d values: 25.2, 8.7, 6.06, 5.04, 4.77, 4.67, 3.60, 3.50

The crystals of this form were prepared by cooling rapidly ethanol-water (80:20 volume ratio) solution of this compound.

Form II d values: 4.85, 4.72, 4.46, 4.37, 4.27, 4.02, 3.97, 3.80, 3.47

The crystals of this form were prepared by crystallizing from ethanol or ethanol-carbon tetrachloride (1:1 volume ratio).

Form III d values: 18.8, 9.4, 6.23, 4.65, 3.69, 3.30, 3.08

The crystals of this form were prepared by crystallizing from ethanol-water (1:1 volume ratio) solution or dioxane-water (1:1 volume ratio) solution.

Form IV d values: 12.0, 6.07, 5.18, 4.37, 4.23, 3.31

The crystals of this form were prepared by crystallizing from dimethyl formamide.

(b) Suspended in 10 ml of ethanol was 2.0 g of hydrochloride of 2-amino-4-[4-(4-chlorobenzyloxy)phenyl]thiazole, and 10 ml of aqueous ammonia was added to the suspension, followed by stirring at room temperature for 10 minutes. Water was added to extract with ethyl acetate. After washing with water and drying, the ethyl acetate was distilled off, thus yielding 1.7 g (94.4%) of 2-amino-4-[4-(4-chlorobenzyloxy)phenyl]thiazole. Recrystallized from ethyl acetate, m.p., 178°–179° C.

The product obtained above can take at least 3 crystal forms. The X-ray diffraction pattern of the product measured by the powder method is as shown below.

Form A d values: 8.85, 5.90, 4.46, 3.80, 3.28

The crystals of this form were prepared by crystallizing from ethyl acetate.

Form B d values: 22.7, 5.75, 4.37, 3.75, 3.22

The crystals of this form were prepared by crystallizing from ethanol.

Form C d values: 4.57, 4.10, 3.80, 3.75, 3.17, 3.00

The crystals of this form were prepared by heating the crystals of form B in the presence of water.

(c) In 30 ml of pyridine was dissolved 2.0 g hydrochloride of 2-amino-4-[4-(4-chlorobenzyloxy)phenyl]thiazole, and 1.0 ml of acetic anhydride was added to the solution, followed by stirring at room temperature for 2 hours. Water was added and, the precipitating crystals were recovered by filtration, thus yielding 1.9 g (95.0%) of 2-acetylamino-4-[4-(4-chlorobenzyloxy)phenyl]thiazole. m.p., 239°–240° C.

(d) Similar treatment with the use of 0.5 ml of acetyl chloride in place of acetic anhydride in the reaction under the item (c) afforded 1.9 g (95.0%) of 2-acetylamino-4-[4-(4-chlorobenzyloxy)phenyl]thiazole.

(e) A mixture of 4-(4-chlorobenzyloxy)phenacyl chloride (2.95 g), thiourea (0.762 g), sodium acetate (0.821 g), water (7 ml) and ethanol (30 ml) was stirred under reflux for 1 hour, cooled and poured into water (100 ml). The resulting crystals were filtered and recrystallized from ethanol (120 ml) to give colorless plates (2.45 g, 77.5%).

melting point: 184° C.–185° C.

crystal form: Form B shown above.

EXAMPLE 2

A 1.43 g portion of 4-(4-chlorobenzyloxy)phenacyl chloride and 495 mg of 1-methylthiourea were stirred in 30 ml of ethanol at 70° C. for 30 minutes. After cooling, 10 ml of aqueous ammonia was added to stir at room temperature for 10 minutes. Water was added to extract with ethyl acetate. After washing with water and drying, the ethyl acetate was distilled off, thus yielding 1.47 g (89.1%) of 4-[4-(4-chlorobenzyloxy)phenyl]-2-methylaminothiazole. Recrystallization from ethyl acetate afforded crystals of m.p. 158°–159° C.

EXAMPLE 3

A 1.0 g portion of 4-(4-chlorobenzyloxy)phenacyl chloride, together with 440 mg of 1-acetylthiourea and 279 mg of sodium acetate, was stirred in 15 ml of ethanol under reflux for 2 hours. After cooling, the precipitated crystals were recovered by filtration, thus yielding 800 mg (65.6%) of 2-acetylamino-4-[4-(4-chlorobenzyloxy)phenyl]thiazole. m.p., 239°–240° C.

EXAMPLE 4

A 1.3 g portion of 4-(4-chlorobenzyloxy)acetophenone and 762 mg of thiourea were finely pulverized and mingled well to add 742 mg of sulfuryl chloride. After stirring at room temperature for 10 minutes, the mixture was heated at 100° C. for 1 hour. After cooling, 10 ml of ethanol was added, and insoluble crystals were recovered by filtration, thus yielding 0.9 g (50.8%) of hydrochloride of 2-amino-4-[4-(4-chlorobenzyloxy)phenyl]thiazole.

EXAMPLE 5

Similar treatment with the use of 1.18 g of 1-acetylthiourea in place of thiourea in Example 4 afforded 1.05 g (65.6%) of 2-acetylamino-4-[4-(4-chlorobenzyloxy)phenyl]thiazole.

EXAMPLE 6

By the same procedures as in Examples 1 through 5, there were obtained the Compound Nos. 1 through 12 shown in Table 1.

TABLE 1

| Compound No. | $(X)_n$ | R | Melting point, °C. (as acid salts) | Solvent for recrystallization | Example No. upon which the procedure was based |
|---|---|---|---|---|---|
| 1 | H | H | 232–234 (HCl) | Methanol | 1, 4 |
| 2 | 2-Cl | H | 195–196 (HBr) | Methanol | 1 |
| 3 | 4-Cl | H | 266–267 (HBr) | Chloroform-methanol | 1 |
| 4 | 4-Cl | —CHO | 194–195 | Chloroform-methanol | 1c |
| 5 | 4-Cl | —COC$_2$H$_5$ | 191–192 | Ethyl acetate | 1c, 5 |
| 6 | 4-Cl | —COC(CH$_3$)$_3$ | 189–190 | Chloroform-methanol | 1d |
| 7 | 4-Cl | —CH$_2$CH=CH$_2$ | 126–127 | Methanol | 2 |
| 8 | 2,4-Cl | H | 226–228 (HCl) | Chloroform-methanol | 1, 4 |
| 9 | 4-F | H | 247–249 (HCl) | 80% ethanol | 1 |
| 10 | 4-CH$_3$ | H | 187–188 | Ethyl acetate | 1 |
| 11 | 3-CF$_3$ | H | 229–231 (HCl) | Methanol | 1 |
| 12 | 3-CF$_3$ | —COC$_2$H$_5$ | 140–141 | Methanol | 1d |

EXAMPLE 7

An example of a practical composition in which the compound of this invention is utilized as a treating agent of for hyperlipemia is as follows:

| (Tablet) | | |
|---|---|---|
| (1) | Hydrochloride of 2-amino-4-[4-(4-chlorobenzyloxy)phenyl]thiazole | 10 mg |
| (2) | lactose | 35 mg |
| (3) | corn starch | 170 mg |
| (4) | microcrystalline cellulose | 30 mg |
| (5) | magnesium stearate | 5 mg |
| | | 250 mg per tablet |

(1), (2), (3) and $\frac{2}{3}$ quantity of (4) are thoroughly mixed, and then the mixture is granulated. Remaining $\frac{1}{3}$ quantity of (4), and (5) are added to the granules and compressed into tablets. Thus prepared tablets can further be coated with a suitable coating agent.

BIOLOGICAL TEST

Usually, 7- to 9-week-old, male ExHC rats were used and divided into well-matched groups so that there might not be produced any difference in average body weight from the control group for each of the groups (groups each consisting of 5 animals). Groups of rats were fed ad libitum intake for 4 days (or 7 days) to a high cholesterol (CH) diet prepared by adding to a CE-2 powdered feed 1% CH, 0.2% sodium cholate and 5% olive oil or a high CH diet containing 0.005 to 0.01% of each of the test samples, and blood samples were then taken from the tail vein to determine levels of plasma CH, apolipoprotein A-1 (apo A-1) and HDL. Plasma CH was assayed according to the Abell method, while apo A-1 and HDL assayed by radio-immunoassay and disk-electrophoresis, respectively. The intensity of each action was expressed in terms of % against the values for the control group, whereby not more than 100% in CH, and not less than 100% both in apo A-1 and HDL were assessed to be the desirable effect. For values of CH and apo A-1, the significant differences were evaluated using a t-test, whereas a t-test was not conducted for HDL which had been analyzed with plasma pooled for each group.

The results are as shown in Table 2.

TABLE 2

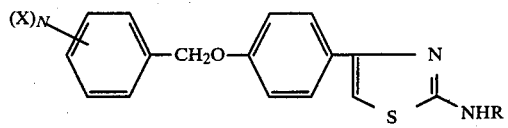

| $(X)_n$ | R | Doses (content in feed, %) | Period of Breeding (days) | Cholesterol | Apo A-1 | HDL |
|---|---|---|---|---|---|---|
| H | H | 0.01 | 4 | 73* | 109 | 135 |
| 2-Cl | H | 0.01 | 4 | 68* | 123* | 162 |
| 4-Cl | H | 0.01 | 4 | 44*** | 137** | — |
| 4-Cl | H(HBr salt) | 0.01 | 4 | 53*** | 141** | 180 |
| 4-Cl | H(HCl salt) | 0.01 | 7 | 47*** | 204*** | 260 |
| 4-Cl | CHO | 0.01 | 7 | 48*** | 193*** | 300 |
| 4-Cl | COCH$_3$ | 0.01 | 4 | 75*** | 147** | 155 |
| 4-Cl | COC$_2$H$_5$ | 0.01 | 4 | 59*** | 148** | 168 |
| 4-Cl | COC(CH$_3$)$_3$ | 0.01 | 4 | 96 | 132* | 104 |
| 4-Cl | CH$_3$ | 0.01 | 4 | 63*** | 127 | 158 |
| 4-Cl | CH$_2$CH=CH$_2$ | 0.01 | 4 | 85 | 160*** | 150 |
| 2,4-Cl | H | 0.005 | 4 | 62** | 108 | 157 |
| 4-F | H | 0.01 | 4 | 47** | 132 | 215 |
| 4-CH$_3$ | H | 0.01 | 4 | 72*** | 109 | 136 |
| 3-CF$_3$ | H | 0.01 | 4 | 52*** | 129 | 205 |
| 3-CF$_3$ | COC$_2$H$_5$ | 0.01 | 4 | 61** | 122** | 164 |

Remarks:
The significant difference from the control group observed for P ≦ 0.05 (*), 0.01 () and 0.001 (*).

What is claimed is:

1. A compound of the formula:

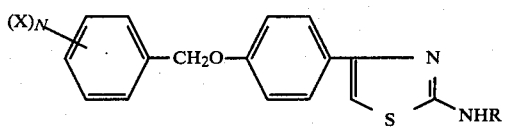

wherein X is hydrogen, halogen, alkyl having 1 to 4 carbon atoms or trifluoromethyl; R is hydrogen, alkyl having 1 to 4 carbon atoms, alkenyl having 2 to 4 carbon atoms, formyl or alkylcarbonyl having 2 to 6 carbon atoms; and n is 1 or 2, or a pharmaceutically acceptable salt thereof.

2. A compound as claimed in claim 1, wherein R is hydrogen.

3. A compound as claimed in claim 1, wherein R is alkylcarbonyl having 2 to 6 carbon atoms.

4. A compound as claimed in claim 1, wherein X is a halogen atom.

5. The compound as claimed in claim 1, wherein the compound is 2-amino-4-[4-(4-chlorobenzyloxy)phenyl]thiazole.

6. The compound as claimed in claim 1, wherein the compound is 2-acetylamino-4-[4-(4-chlorobenzyloxy)phenyl]thiazole.

7. The compound as claimed in claim 1, wherein the compound is 4-[4-(4-chlorobenzyloxy)phenyl]-2-propionylaminothiazole.

8. A pharmaceutical composition which contains an effective amount, for the therapy of hyperlipemia in mammals, of a compound of the formula:

wherein X is hydrogen, halogen, alkyl having 1 to 4 carbon atoms or trifluoromethyl; R is hydrogen, alkyl having 1 to 4 carbon atoms, alkenyl having 2 to 4 carbon atoms, formyl or alkylcarbonyl having 2 to 6 carbon atoms; and n is 1 or 2, or a pharmaceutically acceptable salt thereof, and a pharmaceutically acceptable carrier, vehicle or diluent therefor.

* * * * *